(12) United States Patent
Heinisch et al.

(10) Patent No.: US 6,380,181 B1
(45) Date of Patent: Apr. 30, 2002

(54) SYNTHETIC CATECHOL DERIVATIVES, METHOD FOR PRODUCTION AND USE THEREOF

(75) Inventors: Lothar Heinisch; Ute Moellmann; Matthias Schnabelrauch, all of Jena; Rolf Reissbrodt, Wernigerode, all of (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 09/202,955

(22) PCT Filed: May 14, 1997

(86) PCT No.: PCT/EP97/02453

§ 371 Date: Sep. 10, 1999

§ 102(e) Date: Sep. 10, 1999

(87) PCT Pub. No.: WO97/49670

PCT Pub. Date: Dec. 31, 1997

(30) Foreign Application Priority Data

Jun. 26, 1996 (DE) .......................... 196 25 524

(51) Int. Cl.$^7$ ...................... A61K 31/43; A61K 31/545; A61K 31/195; C07C 69/60
(52) U.S. Cl. ...................... 514/198; 514/192; 514/197; 514/200; 514/563; 514/564; 514/567; 560/138; 560/142; 562/444
(58) Field of Search .......................... 548/178; 560/138; 560/142; 562/444; 514/192, 197, 198, 200, 563, 564, 567

(56) References Cited

U.S. PATENT DOCUMENTS

| | | |
|---|---|---|
| 4,578,404 A | 3/1986 | Takita et al. |
| 4,610,824 A | 9/1986 | Truener |
| 5,580,956 A | * 12/1996 | Saito et al. ................. 530/325 |

FOREIGN PATENT DOCUMENTS

| | | |
|---|---|---|
| DE | 34 14 049 | 10/1984 |
| DE | 42 31 295 | 9/1992 |
| DE | 43 13 946 | 4/1993 |
| EP | 092 722 | 4/1983 |
| EP | 544 166 | 11/1992 |

OTHER PUBLICATIONS

Ohi, N, et al "Semisynthetic beta–Lactam Antibiotics: I. Synthesis and Antibacterial Activity . . . " J. Antibiotics vol. 39 pp 230–241, 1986.*

Winkelmann, G. et al. "HPLC separation of enterobactin and linear 2,3–dihydroxybenzoylserine derivatives" BioMetals, vol. 7, pp. 149–154.*

Kozlowski, H. et al. "Coordination of Copper (II) ions to catechoyl/–dipeptides . . . " J. Inorg. Biochem. vol. 43, pp. 775–787.*

Nakonieczna, L. et al. "Catechoyl–Dipeptides as leucine aminopeptidase inhibitors" Z. Naturforsch. vol. 44b, pp. 811–816.*

Chemical Abstracts, vol. 24: 317711q, No. 23, p. 1275 (1996).

Chemical Abstracts, vol. 118: 109549s (1993).

Heinisch, L., et al. "Synthese und antibakterielle Wirksamkeit von Benzoylaminoacyl–Penicillinen und verwandten Verbindungen mit und ohne acylierte CatecholSubstituenten" (1992). *Arzneim. Forsch/ Drug Res.* 42:668–673.

Smith, P.W., et al. "Synthesis and Biological Activity of Novel Cephalosporins Containing a (Z)–Vinyl Dimethylphosphonate Group" (1995). *The Journal of Antibiotics* 48:73–81.

Pu, Y., et al. "Synthesis, Stability, and Antimicrobial Activity of (+)–Obafluorin and Related β–lactone Antibiotics" (1994). *J. Org. Chem.* 59:3642–3655.

Dolence, E., et al. "Synthesis and Siderophore and Antibacterial Activity of $N^5$–Acetyl–$N^5$–hydroxyl–L–orinthine–Derived Siderophore–β–Lactam Conjugates: Iron–Transport–Mediated Drug Delivery" (1991). *J. Med. Chem.* 34:968–978.

Basker, M., et al. "Antibacterial Activity of Catecholic Piperacillin Analogues" (1989). *The Journal of Antibiotics* 42:1328–1330.

Ohi, N., et al., "Semisynthetic β–Lactam Antibiotics. IV. Synthesis and Antibacterial Activity of New Ureidocephalosporin and Ureidocephamycin Derivatives Containing a Catechol Moiety or Its Acetate" (1987). *Chem. Pharm. Bull.* 35:1903–1909.

Ohi, N., et al. "Semisynthetic β–Lactam Antibiotics. II. Effect on Antibacterial Activity of Ureido N–Substituents in the 6–[(R) –2–[3–(3,4–dihydroxybenzoyl)–1–ureido]2–phenylacetamido]penicillanic acids" (1986). *The Journal of Antibiotics* 39:242–250.

Chemical Abstracts, vol. 78: 145034j, (1973).

Chemical Abstrats, vol. 115: 78765r, (1991).

Chemical Abstracts, vol. 117: 127959j, (1992).

(List continued on next page.)

Primary Examiner—Kathleen K. Fonda
Assistant Examiner—Leigh C. Maier
(74) Attorney, Agent, or Firm—Crowell & Moring LLP

(57) ABSTRACT

Catechol derivatives of general formula (I)

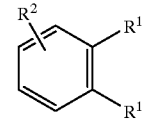

in which $R^1$ denotes O-acyl and $R^2$ represents amino acid residues in the 3- and/or 4-position function as siderophores and/or as biological chelating agents for iron in gram-negative bacteria. Conjugates with antibiotics improve penetration into bacterial cells, thereby increasing antibacterial efficacy of the cells.

19 Claims, No Drawings

OTHER PUBLICATIONS

Higashi, K., et al. "Cutinostatin B as a New Cutinase Inhibitor Produced by Actinomycete" (1996) *Biosci. Biotech. Biochem.* 60:401–404.

Buckley, G., et al. "New Synthetic Probes of the Iron Transport System of *Paracoccus denitrificans*" (1994). *Tetrahedron* 50:11781–11792.

Tor, Y., et al. "Chiral Siderophore Analogs: Enterobactin" (1992). *J. Am. Chem. Soc.* 114:6661–6671.

Bergeron, R., et al. "Short Synthesis of Parabactin" (1982). *J. Am. Chem. Soc.* 104:4489–4492.

Hantke, K., (1990) "Dihydroxybenzolyserine–A Siderophore for *E. coli*", *FEMS Microbiology Letters* 67:5–8.

Ito, T. and Neilands, J.B., (1958) "Products of Low–Iron Fermentation with *Bactillus subtilis*: Isolation, Characterization and Synthesis of 2,3–Dihydroxybenzoylglycine[1,2]", *J Amer. Chem. Soc.* 80:4645–4647.

Kanai, F., Kaneko, T., Morishima, H., Isshiki, K., Takita, T., Takeuchi, T., and Umezawa H., (1985) "Vanoxonin, a New Inhibitor of Thymidylate Synthetase III. Inhibition of Thymidylate Synthetase by Vanoxonin–Vanadium Complex". *The Journal of Antibiotics* 38:39–50.

Corbin, J., and Bulen, W., (1969) "The Isolation and Identification of 2,3–Dihydroxybenzoic Acid and 2–N, 6–N–Di–(2,3–dihydroxybenzoyl)–L–Lysine Formed by Iron–Deficient *Azotobacter vinelandii*", *Biochemistry* 8:757–762.

McKee, J., Sharma, S., Miller, M., (1991) "Iron Transport Mediated Drug Delivery Systems: Synthesis and Antibacterial Activity of Spermidine and Lysine–Based Siderophore–β–Lactam Conjugates". *Bioconjugate Chemistry* 2:281–291.

Chimiak, A., and Neilands, J.B., (1984) "Lysine Analogues of Siderophores". *Structure and Bonding* 58:90–96.

Reissbrot, R., Heinisch, L., Moellmann, U., Rabsch, W., Ulbricht, H., (1993) "Growth Promotion of Synthetic Catecholate Derivatives on Gram–Negative Bacteria". *BioMetals* 6:155–162.

Wolf, H., (1910) "Ueber Kondensationsprodukte der Anthranilsaeure mit aromatischen Aldehyden" (On Condensation Products of Anthranilic Acid with Aromatic Aldehydes). *Monatsh. Chem.* 31:903–16.

Arisawa, M., Sekine, Y., Shimizu, S., Takano, H., Angehrn, P., and Then, R.L., (1991) "In Vitro and In Vivo Evaluation of Ro 09–1428, a New Parenteral Cephalosporin with High Antipseudomonal Activity". *Antimicrob. Agents Chemother.* 35:653–659.

Schwyn, B. and Neilands, J.B., (1987) "Universal Chemical Assay for the Detection and Determination of Siderophores", *Analytical Biochemistry* 160:47–56.

\* cited by examiner

SYNTHETIC CATECHOL DERIVATIVES, METHOD FOR PRODUCTION AND USE THEREOF

The present invention relates to new synthetic catechol derivatives, in which aromatic azomethine-carboxylic acids, benzhydrazones, amino acids, aminobenzoic acids or dipeptides, pyrrolidine- or oxazolidine-carboxylic acids, or formylcarboxymethyloximes function as structural elements, and relates to conjugates thereof with active ingredients, particularly antibiotics.

It is known that certain catechol structures play an essential role as iron-complexing structural elements in natural siderophores ("Iron Transport in Microbes, Plants and Animals", Eds.: Winkelmann, G., van Helm, D., Neilands, J. B., V. Ch.—Verlagsgesellschaft Weinheim, 1987), e.g. enterobactin, which is a siderophore for E. coli and other bacterial strains, is a trimer of N-(2,3-dihydroxybenzoyl)-L-serine. The monomer is also effective as a siderophore (Hantke, K., FEMS Microbiol. Lett. 67 (1990), 5). N-(2,3-dihydroxybenzoyl)glycine has been found to be a siderophore for B. subtilis (Ito, T., Neilands, J. B., J. Amer. Chem. Soc. 80 (1958), 4645). Some catechol-substituted amino acid derivatives have already been produced synthetically, e.g. N-(2.3-dihydroxy-benzoyl)-L-threonine (Kanai, F., Kaneko, T., Morishima, H., Isshiki, K., Taketa. T., Takeuchi, T., Umezawa, H., J. Antibiot. 38 (1985), 39), $N^2$, $N^6$-bis-(2,3-dihydroxybenzoyl)-L-lysine (Corbin, J. L., Bulen, W. A., Biochemistry 8 (1969), 757; McKee, J. A., Sharma, S. K., Miller, M. J., Bioconjugate Chem. 2 (1991) 281), and $N^2$,$N^6$-bis-(2,3-dihydroxybenzoyl)-lysyl-$N^6$-(2,3-dihydroxybenzoyl)lysine (Chimiak, A., Neilands, J. B., Structure and Bonding 58, (1984), 89). It is also known that certain glyoxylic acid benzhydrazones, oxanilic acid derivatives, etc., can serve as siderophores for different bacterial strains (Reissbrodt, R., Heinishe, L., Möllmann, U., Rabsch, W., Ulbricht, H., BioMetals 6 (1993), 155). Some dihydroxybenzylidene-aminobenzoic acids have already been described in the literature, but without any mention of their efficacy as siderophores (Takita, H., Noda, S., Inada. K., Mukaida, Y. S., Toji. M. K., Kobayashi, H., DE 3 414 049 (1984); H. Wolf, Monatsh. Chem. 31 (1910), 903).

Although various catechol compounds have been bonded to β-lactams, by means of which an increase in the antibacterial efficacy of these antibiotics has been achieved due to their transfer into the bacterial cell via bacterial transport routes for iron (e.g. Arisawa, M., Sekine, Y., Shimizu, S., Takano, H., Angehrn, P., Then, R. L., Antimicrob. Agents Chemother. 35 (1991), 653), there is a great need for other new synthetic siderophores with improved pharmacological and pharmaco-kinetic properties, which are suitable for forming conjugates with antibiotics.

On the other hand, as chelating agents for iron, siderophores are potentially capable of influencing the biological metabolism of iron, and diseases associated therewith, in various ways. Thus the siderophore desferrioxamine (desferal) is successfully used in diseases which are caused by an excess of iron (e.g. thalassaemia).

The underlying object of the present invention is to discover new synthetic catechol derivatives which comprise aromatic azomethine-carboxylic acids, benzhydrazones, amino acids, aminobenzoic acids or dipeptides, pyrrolidine- or oxazolidine-carboxylic acids, and formylcarboxymethyloximes as basic structures, which can function as siderophores and/or as biological chelating agents for iron, and which in the form of their conjugates with active ingredients, e.g. antibiotics, effect improved penetration of these compounds into bacterial cells and thereby increase the antibacterial efficacy thereof, and which make it possible to combat penetration-related resistance to antibiotics in bacterial infections in an improved manner.

The compounds according to the invention are effective as siderophores for gram-negative bacteria, i.e. they can supply bacteria with iron ions, and, in die form of their conjugates with active ingredients, e.g. with antibiotics (as "siderophore-antibiotic conjugates"), can transfer these compounds into the bacterial cell via iron transport routes and can thereby improve or even extend the efficacy thereof.

Moreover, the compounds according to the invention are more effective and can be produced more easily than previously known compounds, and in die form of their conjugates with active ingredients make it possible to combat penetration-related resistance to antibiotics in bacterial infections in an improved manner. Furthermore, the present invention provides new chelating agents for iron, which can influence the biological metabolism of iron and which can thus influence diseases associated therewith in various ways.

New synthetic catechol derivatives are provided, of general formula I

Formula I

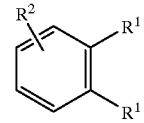

wherein the $R^1$ radicals are identical to or independent of each other and denote OH and/or Oacyl, and $R^2$ represents the following groups in the 3- and/or 4-position:

a. aromatic azomethine-carboxylic acid residues and/or azobenzene-carboxylic acid residues:

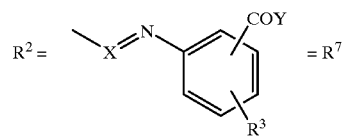

X=CM, N, CH=CH-CH

Y=OA, where A=H, alkyl, aryl, aralkyl, an alkali metal ion (preferably Na, K), an ammonium ion or a substituted ammonium ion, or Y=an active ingredient residue which contains an OH or NH group, $R^3$=one or two Oacyl radicals when $R^1$=OH or Oacyl, or $R^3$=H when $R^1$=Oacyl, or

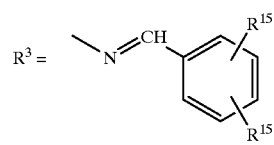

$R^{15}$=radicals which, identically to or independently of each other, represent H and/or Oacyl, or $R^2 =$ [structure with N=CH, benzene ring bearing COY and $R^3$, $R^3$] $= R^8$ Y=OA, where A=H, alkyl, aryl, aralkyl, an alkali metal ion (preferably Na, K), an ammonium ion or a substituted ammonium ion, or Y=an active ingredient residue which contains an OH or NH group, $R^3$=radicals which, identically to or independently of each other, denote H, OH, Oacyl, b. benzhydrazone radicals:

$R^2 =$ [structure] $= R^9$ $R^{15}$=radicals which, identically to or independently of each other, denote H, OH, Oacyl, $R^4$ and/or $R^5$ is H or COY, wherein Y=OA, with A=H, alkyl, aryl, aralkyl, an alkali metal ion (preferably Na, K), an ammonium ion or a substituted ammonium ion, or Y=an active ingredient residue which contains an OH or NH group, c. aminobenzoic acid residues $R^2 =$ [structure] $= R^{10}$ Y=OA, where A=H, alkyl, aryl, aralkyl, an alkali metal ion (preferably Na, K), an ammonium ion or a substituted ammonium ion, or Y=an active ingredient residue which contains an OH or NH group, $R^{19}$=H, alkyl, $R^{20}$=H, alkyl, halogen, OH, Oalkyl, Oacyl, or $R^{20} =$ [structure]

$R^{19}$ and $R^{21}$, identically to or independently of each other, each denote H, OH, Oacyl or Oalkyl in the 2,3- and/or 3,4-position d. amino acid residues:

$R^2 =$ [structure with NH-CH($R^6$)-COY] $= R^{11}$

Y=OA, where A=H, alkyl, aryl, aralkyl, an alkali metal ion (preferably Na, K), an ammonium ion or a substituted ammonium ion, or Y=an active ingredient residue which contains an OH or NH group, $R^6$=alkyl, hydroxyalkyl (comprising $C_1$–$C_5$ when $R^1$=Oacyl and $C_3$–$C_5$ when $R^1$=OH), or alkoxyalkyl, acyloxyalkyl, arylalkoxyalkyl, or $R^6 =$ —$(CH_2)_n$—NH— [structure] $= R^{12}$ $R^{15}$ represents, identically to or independently of each other, H, OH, Oacyl, n is an integer between 1 and 5 when $R^1$ is Oacyl and $R^{15}$ is H and/or Oacyl, or n is an integer between 1 and 3 when $R^1$ is OH and $R^{15}$ is H and/or OH, or $R^6 =$ —$(CH_2)_{n1}$— [structure] —$(CH_2)_{n2}$—NH— [structure] $= R^{13}$ $R^{15}$=radicals which, identically to or independently of each other, denote H, OH, Oacyl, $n_1$ and $n_2$ represent an integer between 1 and 5, e. pyrrolidine- and/or oxazolidine-carboxylic acid residues $R^2 =$ [structure] $= R^{14}$

Z=O, $CH_2$, $R^{16}$ and $R^{17}$, independently of each other, denote H, alkyl or aryl, Y=OA where A=H, alkyl, aryl, aralkyl, an alkali metal ion (preferably Na, K), an ammonium ion or a substituted ammonium ion, or Y=an active ingredient residue which contains an NH or OH group, f. formyl-O-carboxymethyloximes
$R^2$=CH=NOCH$_2$COY, where Y=OA, where A=H, alkyl, aryl, aralkyl, an alkali metal ion (preferably Na, K), an ammonium ion or a substituted ammonium ion, or Y=an active ingredient residue which contains an OH or NH group.

In the above formulae and hereinafter, the term "acyl" denotes a straight-chain or branched $C_1$–$C_6$ alkanoyl or a straight-chain or branched $C_1$–$C_6$ alkoxy-carbonyl. A straight-chain or branched alkyl and a straight-chain or branched alkoxy, also in compound words such as alkoxyalkyl or acyloxyalkyl, denote a straight-chain or branched $C_1$–$C_8$ alkyl or -alkoxy in particular. Aryl denotes phenyl and substituted phenyl in particular, such as a phenyl which is substituted by a straight-chain or branched alkyl, by a halogen, particularly Cl or F, by a straight-chain or branched alkoxy, hydroxy or carboxy, or by a straight-chain or branched alkoxycarbonyl, by a halogen-substituted alkyl or a substituted phenyl, and aralkyl denotes phenylmethyl and 1- or 2-phenylethyl in particular. The cited radicals $R^3$, $R^5$, $R^{15}$, $R^{20}$ and COY may be situated in all possible positions. A substituted ammonium ion is an ammonium ion which is substituted by an alkyl, for example.

The term "active ingredient residue" denotes the residue of any suitable antibacterial active ingredient comprising a free NH or OH group, for example, wherein the active ingredient is esterified or converted to an amide with the catechol radical via this NH or OH group. The bond between the catechol derivative and the antibiotic can be formed either directly or via customary linker groups, e.g. aminocarboxylic acids, hydroxycarboxylic acids, diamines or diols. The term "antibiotic" is to be understood, for example, as a corresponding β-lactam containing an NH or OH group, e.g. a cephalosporin, e.g. cephalexin, cephadroxil or claforan, or a penicillin, e.g. ampicillin or amoxicillin, or a tetracycline derivative, e.g. an aminodioxycycline, or an antibiotic of die aminoglycoside, macrolide, quinolone or carbapenem type.

If asymmetric C atoms are present, the invention likewise relates to the corresponding D- and L- forms, enantiomers and diastereomers, and to racemates and mixtures of enantiomers and diastereomers.

The compounds according to the invention can be prepared for example, by a. the reaction of catechol-substituted benzaldehydes (formula I, where $R^2$=CHO), in a suitable solvent such as ethanol or toluene, with a water trap or with water-bonding means such as a molecular sieve in a soxhlet attachment, at reaction temperatures between +50° C. and +120° C. and generally at the boiling point of the solvent, with corresponding aminobenzoic acids to form aromatic azomethine-carboxylic acids (formula I, where $R^2$=$R^7$ or $R^8$), or by b. the reaction of catechol-substituted benzhydrazides (formula I, where $R^2$=CONHNH$_2$), in a suitable solvent such as water, ethanol or acetic acid, at temperatures between +10° C. and +120° C. and preferably at the boiling point of the solvent, with corresponding formylbenzoic acids or with phenylglyoxylic acids to form corresponding benzhydrazones (formula I, where $R^2$=$R^9$), or by c. the reaction of di(acyloxy)benzoyl chlorides (formula I, where $R^1$=OCOCH$_3$ and $R^2$=COCl, for example) with aminobenzoic acids or esters thereof, in a suitable solvent such as tetrahydrofuran together with a tertiary amine e.g. triethylamine, at a temperature between –30° C. and +20° C., or in aqueous sodium bicarbonate solution at 0° C. to 10° C. to form N-[di(acyloxy) benzoyl] aminobenzoic acids or esters, and the last-mentioned esters are optionally converted into the free acids (formula I, where $R^2$=$R^{10}$), or by d. the reaction of 2,3-di(benzyloxy)benzoyl chloride (formula I, where $R^1$=OCH$_2$C$_6$H$_5$ and $R^2$=COCl), in a suitable solvent such as tetrahydrofuran together with a tertiary amine e.g. triethylamine, at a temperature between –30° C. and +20° C., or in aqueous sodium bicarbonate solution at 0° C. to +10° C., with amino acids, diamino acids or dipeptides, to form the corresponding, protected N-[2,3-di(benzyloxy)-benzoyl]-amino acids, and die latter are then converted, by customary methods of removing the protective groups, for example by catalytic hydrogenation in ethanol, into the free catechol-substituted amino acid derivatives or peptide derivatives (formula I, where $R^2$=$R^{11}$, $R^{12}$, $R^{13}$ or $R^{14}$, wherein Z=CH$_2$), or by e. the reaction of dihydroxy- or diacyloxybenzoyl chloride (formula I, where $R^1$=OH or Oacyl and $R^2$=COCl) with an oxazolidine carboxylate, obtained by known methods from serine and aldehydes, for example formaldehyde, in aqueous alkaline solution, with subsequent acidification in a suitable solvent, for example in ethanol or in an ethanol/water mixture, at a temperature between—10° C. and +10° C., to form substituted oxazolidine,-carboxylic acid derivatives (formula I, where $R^2$=$R^{14}$ and Z=O), or by f. the reaction of catechol-substituted benzaldehyde (formula I, where $R^2$=CHO), in a suitable solvent, with O-carboxymethylhydroxylamine or salts thereof to form the corresponding formyl-O-carboxymethyloximes (formula I, where $R^2$=CH=NOCH$_2$COOH).

The compounds of formula I according to the invention in which Y in $R^2$=an active ingredient residue which comprises a free NH or OH group are prepared, for example, by the reaction of a compound of formula I in which Y in $R^2$=OH, e.g. by the mixed anhydride method, firstly with chloroformic acid ester and a tertiary amine, e.g. triethylamine, and then with the corresponding active ingredient which contains a free NH or OH group and which optionally contains a customary linker group, such as residues of a diamino carboxylic acid, of a hydroxycarboxylic acid or of a diamine or diol, together with a suitable tertiary amine, e.g. triethylamine, in a suitable solvent, e.g. tetrahydrofuran.

The compounds of formula I which contain a carboxyl group may exist as free acids, in the form of their salts or as readily cleavable esters, particularly esters which can be cleaved under physiological conditions. The compounds are purified by the usual methods known from the prior art, for example by recrystallisation or by means of chromatographic methods.

The compounds according to the invention are effective as siderophores for various gram-negative bacterial strains.

Testing for siderophore efficacy was performed using various bacterial indicator mutants which only exhibit reduced growth due to lack of siderophores and which are capable of an increase in growth after the addition of the test substances as substitute siderophores. In the indicator mutants, the synthesis of the respective siderophores, e.g. pyoverdin, pyochelin, enterobactin, aerobactin or yersiniabactin, or the biosynthesis of aromatic compounds, is blocked, or there is a lack of receptors for enterobactin, pyochelin or pyoverdin and for other important components for the bacterial transport of iron (e.g. the membrane proteins Cir, Fiu, FepA and TonB). Under conditions where there is a lack of iron, these mutants therefore cannot grow or can only grow to a very slight extent. In particular, the following indicator mutants were used: Pseudomonas aeruginosa PAO 6609, K 407, 690; E. coli AB 2847, Salmonella typhimurium enb-7, TA 270; Klebsiella pneumoniae KN 4401; Yersinia enterocolitica WAH; Proteus mirabilis 12 (wild); Proteus vulgaris 718 (wild) and Morganella morganii SBK3 (wild). The wild strains denoted by "wild" only possess iron absorption systems which are inadequate, which is why the addition of a siderophore results in increased growth. The controls used were ferrioxamine E for the Pseudomonas strains, ferrioxamine G and enterobactin for the Salmonella strains, ferrichrome for the E. coli, Klebsiella and Y. enterocol. strains, and 3,4-dihydroxybenzylidene-2,4,6-trimethylaniline for Morganella morganii (see the above literature reference by R. Reissbrodt et al.).

For the E. coli mutants IR 112 and H 1728 lacking the membrane proteins TonB or Cir and Fiu, which are important for active iron transport, all the substances tested had no effect. This is an indication that the substances act purely as siderophores.

The growth areas of the indicator mutants (diameter in mm) under the effect of the test substances are given in Tables 1–3. The annotations + and (+) relate to non-specific promotion of growth.

TABLE 1

Growth areas (in mm) of siderophore indicator strains with new synthetic catechol derivatives

| Substance No. | Pseudomonas aeruginosa | | | E. coli | Salmonella typhimurium | |
|---|---|---|---|---|---|---|
| | PAO 6609 | K407 | 690 | AB 2847 | enb-7 | TA 2700 |
| a. | | | | | | |
| 1 | 20 | 16 | 23 | 0 | 35 | 0 |
| 2 | 17 | 18 | 17 | 0 | 30 | 0 |
| 3 | 0 | 0 | 0 | 22 | 28 | 0 |
| 4 | 17 | 18 | 18 | 18 | 34 | 0 |
| 5 | 0 | 0 | 0 | 15 | 0 | 0 |
| 6 | 14 | 17 | 19 | 17 | 34 | 0 |
| 7 | 0 | 0 | 0 | 0 | 0 | 0 |
| 8 | 13 | 15 | 0 | 13 | 0 | 0 |
| b. | | | | | | |
| 9 | | | 10 | 0 | 0 | 0 |
| 10 | 0 | 0 | 0 | | 22 | 20 |
| 11 | 14 | 0 | 12 | 0 | 10 | 0 |
| 12 | 14 | 0 | 12 | 14 | 0 | 0 |
| 13 | 10 | 11 | 10 | | 18 | 23 |
| Control (see text) | 35 | 35 | 40 | 23 | 38 | 20 |

TABLE 2

Growth areas (in mm) of siderophore indicator strains with new synthetic catechol derivatives

| Substance No. | Klebsiella KN 4401 | Y. enterocol. WAH | Proteus mir. 12 | Proteus vul. 718 | M. morg. SBK 3 |
|---|---|---|---|---|---|
| a. | | | | | |
| 1 | 0 | 10 | 26 | 35 | 35 |
| 2 | 35 | 0 | 16 | 25 | 20 |
| 3 | 32 | 0 | 18 | 18 | 20 |
| 4 | 33 | 12 | 23 | 24 | 27 |

TABLE 2-continued

Growth areas (in mm) of siderophore indicator strains with new synthetic catechol derivatives

| Substance No. | Klebsiella KN 4401 | Y. enterocol. WAH | Proteus mir. 12 | Proteus vul. 718 | M. morg. SBK 3 |
|---|---|---|---|---|---|
| 5 | 0 | 0 | 19 | 21 | 21 |
| 6 | 25 | | 23 | 25 | 25 |
| 7 | 23 | 0 | 20 | 22 | 22 |
| 8 | 20 | 12 | 20 | 20 | 20 |
| b. | | | | | |
| 9 | 27 | 10 | 9 | | |
| 10 | 18 | 26 | 15 | 16 | 16 |
| 11 | 32 | 10 | 15 | 20 | 20 |
| 12 | 30 | 25 | 17 | 20 | 15 |
| 13 | 15 | 10 | 23 | 23 | 24 |
| 14 | 27 | 10 | 10 | 12 | 11 |
| 15 | 0 | 12 | | | 11 |
| Control (see text) | 25 | 26 | 18 | 25 | 18 |

TABLE 3

Growth areas (in mm) of siderophore indicator strains with new synthetic catechol derivatives

| Substance No. | P. aeruginosa | | | E. coli | S. typhimurium | | M. morg. |
|---|---|---|---|---|---|---|---|
| | PAO 6609 | K407 | 690 | AB 2847 | enb-7 | TA 2700 | SBK3 |
| c. | | | | | | | |
| 16 | 20 | 20 | 20 | 24 | 25 | 10 | |
| 17 | 0 | | | 26 | 0 | | 12 |
| d. | | | | | | | |
| 18 | 20 | 17 | 18 | 30 | 48 | 50 | |
| 19 | | 10 | 0 | 11 | 29 | 17 | |
| 20 | | 10 | 0 | 18 | 31 | 12 | |
| 21 | 14 | 15 | 15 | 33 | 36 | 40 | |
| 22 | 48 | 40 | | 50 | 0 | 50 | 50 |
| 23 | | | 14 | 22 | 27 | 20 | |
| 24 | 20 | 20 | 20 | 40 | 50 | 40 | |
| 25 | 18 | | | | 30 | 28 | 38 |
| 26 | 0 | | | 14 | 32 | | 10 |
| Control (see text) | 35 | 35 | 40 | 23 | 38 | 20 | |

Due to their properties as bacterial siderophores, the compounds of general formula I can serve as transport vehicles or penetration accelerators for antimicrobial antibiotics and other active ingredients, i.e. in conjugates with antibiotics or other active ingredients they can serve to transport the latter into the microbial cell via iron transport routes and can thus increase their efficacy.

Compounds of general formula I, where Y in $R^2$=an active ingredient residue, possess an antibacterial efficacy, for example even in part against bacteria which are resistant to other β-lactams. Therefore, a few compounds of general formula I, where Y=an active ingredient residue, e.g. substances 28–37, were tested in an agar diffusion test against particular bacterial strains which are in part resistant to other β-lactams (Table 4). The following strains were used: Pseudomonas aeruginosa SG 137 (carbenicillin-resistant), KW 799 WT (wild type), KW 799/61 (penetration mutant, cell wall damaged, penetration made easier), ATCC 27853 (wild type), ATCC 9027 (wild type), NCTC 10662 (ATCC 25668, clinical isolate, carbenicillin-sensitive), NCTC 10701 (carbenicillin-sensitive), NPS1 and Oxa6 (plasmid-coded β-lactamase); *E. coli* DCO (wild type), DC2 (penetration mutant, cell wall damaged, penetration made easier), *Klebsiella pneumoniae* ATCC 10031 (wild type), as well as SG 117; *Salmonella gallinarum* ATCC 9184; *Stenotrophomonas maltophilia* GN 12873 (ampicillin-, azlocillin- and carbapenem-resistant), and IMET 10402.

Surprisingly, it was found that the substances tested exhibited outstanding efficacy, not only for ampicillin-resistant and/or β-lactamase inhibitor-resistant wild type strains, but that they were also effective for two Pseudomonas strains comprising plasmid-coded β-lactamase (NPS1, Oxa6) and multi-resistant Stenotrophomonas strains, whilst azlocillin, and in part meropenem and imipenem also, for example, were ineffective.

The results of the tests are given in Table 5. According to these results, all the siderophore-ampicillin conjugates were highly effective compared with azlocillin and ampicillin as the standards, particularly against *Pseudomonas aeruginosa* SG 137, which is a germ which is particularly resistant to carbenicillin. They were also highly effective against wild type strains of Pseudomonas, and were also effective in part against *E. coli* and Serratia.

With the test germs KW 799/WT and /61 of Pseudomonas and DCO and DC2 of *E. coli*, the effect of improved penetration capacity on the efficacy of the substances was investigated. KW 799/61 and DC2 are mutants which pos-

TABLE 4

Antibacterial efficacy of siderophore-antibiotic conjugates in the agar diffusion test
[concentration 100 µg/ml; inhibition spot diameter in mm].

| | *Pseudomonas aeruginosa* | | | | | | | | |
|---|---|---|---|---|---|---|---|---|---|
| Substance No. | SG 137 | KW799/ WT | KW799/ 61 | ATCC 27853 | ATCC 9027 | NCTC 10662 | NCTC 10701 | NPS 1 | OXA 6 |
| Ampicillin | 0 | 0 | 41 | 0 | 0 | 0 | 0 | 0 | 0 |
| Azlocillin | 17 | 27 | 40 | 19 | 15 | 17 | 27 | 0 | 0 |
| Amoxicillin/ clavulanic acid imipenem | 0 | 0 | 37 | 0 | 0 | 0 | 0 | 0 | 0 |
| 27 | 22 | 30 | 37 | | 19 | 16 | 0 | 10 | 12 |
| 28 | 20 | 27 | 31 | | 18 | 17 | | 18 | 19 |
| 29 | 28 | 27 | 33 | | 21 | | 23 | 12 | 13 |
| 30 | 22 | 27 | 33 | | | | | | |
| 31 | 28 | 27 | 37 | | | | | | |
| Na-31 | 31 | 31 | [38] | 24 | | | | | |
| 32 | 16 | 25 | 32 | | | | | | |
| Na-35 | 31 | 30 | [38] | 22 | | | | | |
| 36 | 25 | 25 | 29 | 19 | | | | | |
| Na-37 | 22 | 28 | 35 | 21 | | | | | |

| | *E. coli* | | *Klebsiella pneumoniae* | | *Stenotrophomonas maltophilia* | | *Salmonella galinarum* |
|---|---|---|---|---|---|---|---|
| | | | ATCC | SG | GN | IMET | ATCC |
| Substance No. | DC2 | DC0 | 10031 | 117 | 12873 | 10402 | 9184 |
| Ampicillin | 32 | 22 | | 19 | 0 | 0 | 34 |
| Azlocillin | 33 | 16 | 15 | 18 | 0 | 21 | 21 |
| Amoxicillin/ clavulanic acid imipenem | 29 | 18 | 21 | 29 | 0 0 | 0 | 34 |
| 27 | 30 | 21 | | 17 | 22 | 29 | 24 |
| 28 | 27 | 23 | | 17 | 20 | 24 | |
| 29 | 28 | 22 | | 15 | 19 | 23 | 22 |
| 30 | 31 | 25 | | | 19 | | 29 |
| 31 | 33 | 27 | | | 23 | | 29 |
| Na-31 | 38 | 28 | 21 | 26 | 29 | | 34 |
| 32 | 28 | 22 | | | 19 | | 28 |
| Na-35 | 38 | 24 | 20 | 23 | 28 | | 33 |
| 36 | 19 | 13 | 17 | 16 | 24 | | 23 |
| Na-37 | 33 | 27 | 22 | 19 | 16 | | 29 |

[ ] at 50 µg/ml

The surprisingly good efficacy was also verified in a microdilution test. The minimum inhibiting concentrations (MICs) were determined for the following bacterial strains: *Pseudomonas aeruginosa* NCTC 10701, NCTC 10662, SG 137, ATCC 27853, KW 799 WT and KW 799/61, *E. coli* DCO, DC2 and ATCC 25922, *Serratia marcescens* SG 621; *Salmonella gallinarum* ATCC 9184, *Klebsiella pneumoniae* ATCC 10031 and SG 117.

sess a more penetrable outer membrane compared with the wild types KW 799/WT and DCO, respectively. For the comparison substances azlocillin and ampicillin, penetration capacities which were poor to a greater or lesser extent were determined from the considerable differences in their activity against the wild type and against mutants. This was in contrast to the behaviour of the conjugates, which exhibited a good penetration capacity.

TABLE 5

Antibacterial efficacy of siderophore-antibiotic conjugates in a microdilution test [MIC values in μg/ml].

| Substance No. | Pseudomonas aeruginosa SG 137 | KW 799/WT | KW 799/61 | ATCC 27853 | NCTC 10662 | NCTC 10701 | E. coli DC2 | DC0 | ATCC 25922 | Serratia marcescens SG 621 | Salmonella gallinarum ATCC9184 | Klebsiella pneumoniae ATCC 10031 | SG 117 | Stenotrophomonas maltophilia GN 12873 |
|---|---|---|---|---|---|---|---|---|---|---|---|---|---|---|
| Ampicillin | >100 | >100 | 0.4 | >100 | >100 | >100 | 1.56 | 6.25 | 6.25 | 25 | 0.2 | 50 | 12.5 | >100 |
| Azlocillin | 6.25 | 3.12 | 0.2 | 6.25 | 6.25 | 0.2 | 0.78 | 12.5 | 6.25 | 50 | 3.12 | 6.25 | 6.25 | 25–100 |
| Amoxicillin/clavulanic acid | >100 | | | >100 | >100 | | | | 6.25 | | | 3.12 | | >100 |
| Meropenem | 0.1 | | | 0.2 | | | | | <0.05 | | | <0.05 | | >100 |
| 27 | 3.12 | 0.78 | 0.2 | 6.25 | | 0.4 | 0.4 | 3.12 | 6.25 | 50 | 1.56 | 0.4 | 50 | |
| 28 | 1.56 | 1.56 | 0.4 | | | 0.78 | 0.4 | 1.56 | | 6.25 | 1.56 | | 25 | |
| 29 | 0.78 | 3.12 | 0.4 | | 12.5 | | 1.56 | 50 | 100 | 25 | | 50 | | 12.5 |
| 30 | 0.4 | 0.78 | 0.2 | | 6.25 | | 0.4 | 6.25 | 6.25 | 50 | | 6.25 | | 3.12 |
| 31 | 0.1 | 0.78 | 0.2 | | 6.25 | | 0.2 | 12.5 | 0.78 | 25 | | 0.4 | | 0.4 |
| Na-31 | 0.1 | | | 0.78 | 0.78 | | | | | 0.2 | | | | 6.25 |
| 32 | 1.56 | 1.56 | 0.4 | | | | 1.56 | 12.5 | | 25 | | | | |
| Na-35 | 0.1 | | | 1.56 | 1.58 | | | | | 0.2 | | | | 6.25 |
| 36 | 0.4 | | | 3.12 | 6.25 | | | | | 25 | | | | 1.56 |
| Na-37 | 0.4 | | | 3.12 | 12.5 | | | | 3.12 | | | 3.12 | | 6.25 |

The results obtained with penetration mutants of Pseudomonas, KW 799/61, and of E. coil DC2 and wild types thereof confirmed that most of the new substances possessed a considerably better penetration capacity than ampicillin and azlocillin. By means of further experiments using special E. coli mutants which lack the porins ompC and ompF, via which β-lactams normally enter the bacterial cell, or which lack the membrane protein tonB, which is essential for the active transport of iron, it was shown that the siderophore-antibiotic conjugates described above are capable of utilising two penetration paths (via the porins ompC and ompF and via the tonB iron transport path), whilst the antibiotic activity of ampicillin and azlocillin depended only on the presence of the porins. The efficacy against β-lactamase formers and against multi-resistant germs is therefore due to a new type of mechanism for overcoming the penetration resistance, by means of which the ratio of active ingredient to enzyme in the bacterial cell is influenced so that not all antibiotic molecules are inactivated before they reach their target.

TABLE 6

Dependence of the antibacterial activity of the new substances on porins and tonB for mutants of E. coli (inhibition spot diameter in agar diffusion test in mm)

| Substance No. | Mutants: KB5 ompC− | KB4 ompF− | PLB3268 ompF++ | BR185 tonB− | AB2847 tonB+ |
|---|---|---|---|---|---|
| 27 | 7.5 | 8.5 | 14 | 1 | 7 |
| 28 | 11 | 11.5 | 13 | 0 | 8.5 |
| 29 | 7 | 9.5 | 14 | 0 | 6 |
| ampicillin | 9.5 | 10 | 17.5 | 12.5 | 12.5 |
| azlocillin | 4 | 6.5 | 17.5 | 8 | 8 |

PLB268: ompF− was super-expressed.

Furthermore, the results of a CAS test are given in Table 7. The CAS test (chromazurol-S test) of Schwyn and Neilands (Anal. Biochem. 160, 47 (1987)) is based on a colour reaction due to the dissolution leaching of Fe from the chromazurol-S complex and its binding by the catechol compound, by means of which the property of the compound as a siderophore is detected. The CAS tests were positive for the new substances, whilst they were completely negative for ampicillin and azlocillin. This also verifies the surprising discovery that the new antibiotics enter the bacterial cell in an enhanced manner, namely via an iron transport route in addition to the porin route.

TABLE 7

Complexing of Fe by the new types of antibiotic (CAS test)

| Substance No. | CAS Test |
|---|---|
| 27 | ++ |
| 28 | ++ |
| 29 | +++ |
| ampicillin | − |
| azlocillin | − |

On account of their properties as siderophores or as chelating agents for iron, compounds of general formula I, and also the salts thereof when acidic groups are present, and also the esters thereof which can cleave under physiological conditions, are suitable for application as drugs for diseases which are caused by a disorder of the physiological metabolism of iron. On account of their antibacterial efficacy, compounds of general formula I in which Y in $R^2$=an active ingredient residue, e.g. the residue of an antibiotic containing an NH or OH group, and also the salts thereof when acidic groups are present, and the esters thereof which can cleave under physiological conditions, are suitable as drugs for combatting bacterial infections in humans and working animals.

Compounds of formula I can be used for said diseases either on their own or in the form of pharmaceutical preparations with physiologically compatible adjuvant or carrier materials which are known in the art, wherein all customary pharmacological forms of application are possible in principle.

EXAMPLES a. Aromatic Azomethine-carboxylic Acids
General Procedure for Examples 1, 2 and 7:

2 mmoles of the respective benzaldehyde and 2 mmoles of the corresponding aminobenzoic acid were heated in 100 ml of dry toluene for 4–5 hours under reflux, with a water separator trap fitted. The crystals which precipitated after cooling to room temperature or after reducing the amount of solvent were filtered off under suction and recrystallised.

General Procedure for Examples 3, 4, 5, 6 and 8:

2 mmoles of the respective benzaldehyde and 2 mmoles of the corresponding aminobenzoic acid (1 mmole for diamino compounds) were heated in 80 ml of dry ethanol for 3–4 hours under reflux. A soxhlet extraction attachment filled with molecular sieve was used for binding the water formed during the reaction. The crystals which precipitated after cooling to room temperature or after reducing the amount of solvent were filtered off under suction and recrystallised.

Example 1

3-[3,4-di(Methoxycarbonyloxy)-benzylideneamino]-benzoic Acid (1)

Formula 1, where $R^1$=OCOOCH$_3$, $R^2$=$R^7$ in the 4-position, with $R^3$=H, COY in the 3-position, and X=CH, Y=OH Substance 1 was obtained by the reaction of 3,4-di(methoxycarbonyloxy)-benzaldehyde and 3-aminobenzoic acid, in a yield of 53% theoretical, as a slightly yellow solid, f.p. 198 to 199° C. (toluene).

Example 2

3-[3,4-di(Methoxycarbonyloxy)-benzylideneamino]4-hydroxybenzoic Acid (2)

Formula I, where $R^1$=OCOOCH$_3$, $R^2$=$R^7$ in the 4-position, with $R^3$=2-OH, COY in the 5-position, X=CH, Y=OH Substance (2) was obtained by the reaction of 3,4-di(methoxycarbonyloxy)-benzaldehyde and 3-amino4-hydroxybenzoic acid, in a yield of 30% theoretical, as a slightly yellow solid with an f.p. of 221 to 223° C. (toluene).

Example 3

3-(2,3-Dihydroxy)benzylideneamino]-4-hydroxybenzoic Acid (3)

Formula I, where $R^1$=OH, $R^2$=$R^7$ in the 3-position, with $R^3$=2-OH, COY in the 5-position, X=CH, Y=OH Substance (3) was obtained by the reaction of 2,3-dihydroxybenzaldehyde and 3-amino-4-hydroxybenzoic acid, in a yield of 59% theoretical, as red crystals with an f.p. of 273 to 274° C. (ethanol).

Example 4

3,5-Bis-[3,4-di(methoxycarbonyloxy)-benzylideneamino]-benzoic Acid (4)

Formula I, where $R^1$=OCOOCH$_3$, $R^2$=$R^7$ in the 4-position, and where

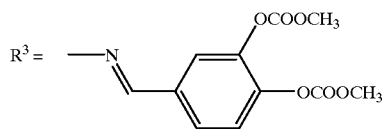

in the 3-position, with COY in the 5-position, X=CH, Y=OH

Substance (4) was obtained by the reaction of 3,4-di(methoxycarbonyloxy)benzaldehyde and 3,5-diaminobenzoic acid, in a yield of 49% theoretical, as a slightly yellow solid with an f.p. of 145 to 148° C. (toluene).

Example 5

4-(2,3-Dihydroxy)benzylideneamino]-3-hydroxybenzoic Acid (5)

Formula I, where $R^1$=OH, $R^2$=$R^7$ in the 3-position, with $R^3$=2-OH, COY in the 4-position, X=CH, Y=OH Substance (5) was obtained by the reaction of 2,3-dihydroxybenzaldehyde and 4-amino-3-hydroxybenzoic acid, in a yield of 85% theoretical, as red crystals with an f.p. of 278 to 280° C. (ethanol).

Example 6

4-(3,4-Diacetoxybenzylideneamino)-benzoic Acid (6)

Formula I, where $R^1$=OCOCH$_3$, $R^2$=$R^7$ in the 4-position, with $R^3$=H, COY in the 4-position, X=CH, Y=OH Substance (6) was obtained by the reaction of 3,4-diacetoxybenzaldehyde and 4-aminobenzoic acid, in a yield of 77% theoretical, as a yellow solid with an f.p. of 180 to 182° C. (toluene).

Example 7

3-[(3,4-Diacetoxyphenylimino)-methyl]-4,5-dihydroxybenzoic Acid (7)

Formula I, where $R^1$OCOCH$_3$, $R^2$=$R^8$ in the 3-position, with $R^3$=2,3-OH, COY in the 5-position, and Y=OH Substance (7) was obtained by the reaction of 3-formyl4,5-dihydroxybenzoic acid and 3,4-di(acetoxy)-aniline, in a yield of 79% theoretical, as red crystals with an f.p. of 240 to 243° C.

$^1$H NMR (dioxane-d$_8$, δ in ppm): 8.79 (s, 1 H, CH=N), 7.76 (s, 1 H, ArH), 7.56 (s, 1 H, ArH), 7.28 (m, 3 H, ArH), 2.26 (s, 3 H, CH$_3$CO), 2.24 (s, 3 H, CH$_3$CO).

Example 8

3-(3,4-Dihydroxyphenylazo)benzoic Acid (8)

Formula I, where $R^1$=OH, $R^2$=$R^7$ in the 4-position, with X=N, $R^3$=H, COY in the 3-position, Y=OH 3-aminobenzoic acid (612 mg, 4.5 mmoles) was diazotised with 312 mg sodium nitrite at 0° C. in 15 ml ethanol and 2.5 ml concentrated hydrochloric acid. A solution of 0.97 g (4.5 mmoles) catechol monobenzoate in 20 ml ethanol was added at 0° C., with stirring, to the solution of the diazonium salt. 5 ml of a 25% Na$_2$CO$_3$ solution was then added to adjust the pH to 9. The reaction mixture was stirred for a further 2 hours at 0° C., adjusted to pH 2 with HCl, and was extracted with dichloromethane. The organic phase was washed with water and dried over sodium sulphate. The crude product obtained after removing the solvent under vacuum was recrystallised from ethanol/water. Yield: 327 mg (28 % theoretical). Red-brown crystals, f.p. 213 to 215° C. (ethanol).

$^1$H NMR (DMSO-d$_6$, δ in ppm, J in Hz): 8.28 (m, 1 H, ArH), 8.04 (dd, J=1.8, 7.8, 2 H, ArH), 7.69 (t, J=7.8, ArH), 7.42 (dd, J=2.3, 8.3 1 H, ArH), 7.36 (d, J=2.3, 1 H, ArH), 6.94 (d, J=8.3, 1 H, ArH).

b. Benzhydrazones

Example 9

[(3,4-Dihydroxybenzoyl)-hydrazono]-phenylacetic Acid (9)

Formula I, where $R^1$=OH, $R^2$=$R^9$ in the 4-position, with $R^4$=COOH, $R^5$=H, $R^{15}$=H 1.2 g phenylglyoxylic acid (0.01 mole) in 5 ml ethanol and 1.7 g 3,4-dihydroxybenzhydrazide (0.01 mole) in 5 ml of 2 N hydrochloric acid were mixed and stirred for 1 hour at room temperature. Colourless crystals (ethanol). Yield 1.18 g (40% theoretical), f.p. 194 to 195° C. (decomposition).

$^1$H NMR (DMSO-d$_6$, δ in ppm): 12.8 (1H, s, NHCO), 6.86 to 7.69 (m, 8H, ArH).

Example 10

4-[(2,3-Dihydroxybenzoyl)-hydrazonomethyl]-benzoic Acid (10)

Formula I, where $R^1$=OH, $R^2$=$R^9$ in the 3-position, with $R^4$, $R^{15}$=H, $R^5$=4-COOH 0.6 g (5 mmoles) terephthalaldehydic acid and 0.85 g (5 mmoles) 2,3-dihydroxybenzhydrazide were boiled for 1 hour under reflux in 10 ml ethanol. Colourless crystals (ethanol/water), yield 909 mg (61% theoretical), f.p. 301 to 302° C.

Example 11

4-[(3,4-Dihydroxybenzoyl)-hydrazonomethyl]-benzoic Acid (11)

Formula I, where $R^1$=OH, $R^2$=$R^9$ in the 4-position, with $R^4$, $R^{15}$=H, $R^5$=4-COOH 0.6 g (5 mmoles) 4-formylbenzoic acid and 0.85 g (5 mmoles) 3,4-dihydroxybenzhydrazide were boiled for 1 hour under reflux in 10 ml ethanol. Colourless crystals, purified by dissolution in dimethylformamide, filtration and precipitation with water, yield 889 mg (61% theoretical), f.p. 314 to 315° C.

Example 12

{[3,4-di(Methoxycarbonyloxy)-benzoyl]-hydrazono}-phenylacetic Acid (12)

Formula I, where $R^1$=OCOOCH$_3$, $R^2$=$R^9$ in the 4-position, with $R^4$=COOH, $R^5$=H, $R^{15}$=H 300 mg (1 mmole) [(3,4-dihydroxybenzoyl)-hydrazono]-phenylacetic acid (1 mmole; =the product from Example 9) were stirred for 10 minutes at 0° C. with 2 ml methyl chloroformate in 2 ml 2 N aqueous sodium hydroxide solution and 3 ml water. The batch was then made alkaline again with 2 N aqueous sodium hydroxide solution, 1 ml methyl chloroformate was added, and the batch was stirred again for 30 minutes. It was then adjusted to pH 2 with 2 N hydrochloric acid. Colourless crystals (from methanol/water), yield 221 mg (53% theoretical), f.p. 171 to 172° C. (decomposition).

$^1$H NMR (DMSO-d$_6$, δ in ppm): 7.4–7.9 (m, 8 H, ArH), 3.87, 3.85 (2×3 H OCOCH$_3$).

Example 13

3-formyl-4,5-dihydroxybenzoic Acid-(2,3-dihydroxy-benzhydrazone) (13)

Formula I, where $R^1$OH, $R^2$=$R^9$ in the 3-position, with $R^5$=5-COOH, $R^4$=H, $R^{15}$=3,4-OH A mixture of 364 mg 3-formyl-4,5-dihydroxybenzoic acid, dissolved in hot water, and 340 mg 2,3-dihydroxybenzhydrazide, dissolved in 5 ml of 2 N hydrochloric acid, was boiled for 10 minutes with stirring. Colourless crystals (glacial acetic acid), yield 431 mg (65% theoretical), f.p. 280–281° C. DC $^1$H NMR (DMSO-D$_6$, δ in ppm): 8.72 (1H, s, CH=N), 6.8–7.6 (5H, ArH), 7.74–7.75 (2×1H, d, J=1.6, 2- or 6 CH of benzoic acid), 7.35–7.39 and 6.98–7.02 (2×1H, d, J=8.4 and 6 CH of benzhydrazone), 6.74–6.82 (1H, t, J=8.5, CH of benzhydrazone).

Example 14

4-{[3,4-di-(Methoxycarbonyloxy)-benzoyl]-hydrazono-methyl}-benzoic Acid (14)

Formula I, where $R^1$=OCOOCH$_3$, $R^2$=$R^9$ in the 4-position, with $R^5$=4-COOH, $R^4$=H, $R^{15}$=H, 300 mg(1 mmole) 4-[(3,4-dihydroxybenzoyl)-hydrazonomethyl]-benzoic acid (=the product from Example 11) were dissolved in 1 ml of 2 N aqueous sodium hydroxide solution and 3 ml water, and the solution was cooled to 0° C. and treated with 2 ml methyl chloroformate with stirring. The mixture was stirred for a further 30 minutes with additional cooling and was then adjusted to pH 3 with HCl. Colourless crystals (ethanol/water), yield 205 mg (49% theoretical), f.p. 184 to 187° C. (decomposition).

1H NMR (DMSO-D$_6$, δ in ppm): 8.50 (s, 1H, CH=N), 7.62–8.04 (m 7H, ArH), 3.88 (s, 6H, 2×OCOOCH$_3$).

Example 15

6-[(3,4-Dihydroxybenzoyl)-hydrazonomethyl]-2,3-dihydroxybenzoic Acid (15)

Formula I, where $R^1$=OH, $R^2$=$R^9$ in the 4-position, with $R^5$=2-COOH, $R^4$=H, $R^{15}$=3,4-OH A mixture of 182 mg (1 mmole) 6-formyl-2,3-dihydroxybenzoic acid, dissolved in hot water, and 168 mg (1 mmole) 3,4-dihydroxybenzhydrazide, dissolved in 5 ml of 2 N hydrochloric acid, was boiled for 10 minutes with stirring. Pale yellow crystals (water). Yield 215 mg (65% theoretical), f.p. 252° C.

1H NMR (DMSO-D$_6$, δ in ppm): 8.53 (s, 1 H, CH=N), 6.8–7.3 (m, 5 H, ArH).

c. Aminobenzoic Acid Derivatives

Example 16

2-(2,3-Diacetoxy-benzoylamino)-benzoic Acid (16)

Formula I, where $R^1$=OCOCH$_3$, $R^2$=$R^{10}$ in the 3-position, with COY in the 2-position, Y=OH, $R^{18}$–$R^{20}$=H Method 1:

1.50 g (0.011 mole) anthranilic acid were slurried in 100 ml of 0.5 M NaHCO$_3$ solution, and were treated at 0 to 10° C., in an ultrasonic bath with stirring, with 2.56 g (0.01 mole) 2.3-diacetoxybenzoyl chloride in 8 ml tetrahydrofuran. The turbid solution which formed after 45 minutes was filtered and carefully acidified with concentrated hydrochloric acid. The colourless crystals obtained were washed with a little ethyl acetate and dried under vacuum. f.p. 203 to 204° C., yield 2.7 g (75% theoretical).

$^1$H NMR (DMSO-D$_6$, δ in ppm): 11.8 (s, 1H, NHCO), 7.2–8.5 (m, 7H, ArH), 2.15 and 2.25 (s, 2×3 H, OCOCH$_3$).

Method 2:

2.57 g 2,3-diacetoxybenzoyl chloride in 50 ml tetrahydrofuran were added at 0° C. to 1.4 g (0.01 mole) anthranilic acid in 100 ml sodium bicarbonate solution. The mixture was reacted for 1 hour at 0–10° C. and then for 30 minutes in an ultrasonic bath at room temperature. It was then partially concentrated and was carefully acidified with 2 N hydrochloric acid. Pale yellow crystals (ethyl acetate), yield 2.3 g (64% theoretical), f.p. 198 to 200° C.

Example 16a

4-[(2,3-Dimethoxycarbonyloxy-benzoyl)-methylamino]benzoic Acid

Formula I, where $R^1$=OCOOCH$_3$, $R^2$=$R^{10}$ in the 3-position, $R^{19}$=CH$_3$, $R^{18}$=$R^{20}$=H, COY in the 4-position, Y=OH Using method 1, the title compound was obtained analogously from 4-methylaminobenzoic acid and 2,3-di-(methoxy-carbonyloxy)-benzoyl chloride, in a yield of 65% theoretical.

Example 16b 3,5-bis-(2,3-Diacetoxybenzoylamino)-benzoic Acid

Formula I, where $R^1$=OCOCH$_3$, $R^2$=$R^{10}$ in the 3-position, $R^{18}$=$R^{19}$=H, $R^{20}$=(2,3-diacetoxy)-benzoylamino in the 5-position with COY in the 3-position, Y=OH Using method 1, the title compound was obtained analogously from 3,5-diaminobenzoic acid and 2,3-diacetoxy)-benzoyl chloride, in a yield of 55% theoretical.

Example 17

4-(2,3-Diacetoxy-benzoylamino)benzoic Acid (17)

Formula I, where $R^1$=OCOCH$_3$, $R^2$=$R^{10}$ in the 3-position, with COY in the 4-position, Y=OH, $R^{18}$–$R^{20}$=H 257 mg 2,3-diacetoxybenzoyl chloride in 5 ml tetrahydrofuran were added to 137 mg (1 mmole) 4-aminobenzoic acid and 0.14 ml triethylamine in 10 ml tetrahydrofuran. The mixture was stirred for 30 minutes at 20° C. and then for 30 minutes at room temperature. It was then partially concentrated and was carefully acidified with 2 N hydrochloric acid. Pale yellow crystals (ethyl acetate), yield 215 mg (60% theoretical). f.p. 134–135° C.

$^1$H NMR (DMSO-D$_6$, δ in ppm): 7.3–7.9 (m 7 H, ArH), 2.1 and 2.3 (s, 2×3 H, OCOCH$_3$).

d. Amino Acid Derivatives

General Procedure for Examples 19, 20, 22, 23 and 25:

1st Step (acylation):

2.5 mmoles of the respective amino acid or dipeptide (present in its free form or as the hydrochloride or acetate) were dissolved in 10 ml of aqueous NaOH solution (2.5 mmoles NaOH for alanine, 7.6 mmoles for diamino acids, 11.5 mmoles for the dipeptide). A solution of 2,3-di(benzyloxy)-benzoyl chloride (2.5 mmoles for alanine, 5.1 mmoles for diamino acids, 9 mmoles for the dipeptide) in 10 ml THF was slowly added drop-wise at 0° C. with stirring, followed by warming to 20 to 25° C. when the addition was complete. The reaction mixture was stirred for 4 hours at this temperature and was subsequently adjusted to pH 2 with 2 M HCl. The reaction mixture was extracted with ethyl acetate, the organic phase was washed with saturated aqueous sodium chloride solution and dried over sodium sulphate, and the solvent was removed under vacuum. The crude product could be purified by recrystallisation (ethanol/water in the case of the alanine derivative) or by column chromatography (silica gel 60, Merck, eluent:chloroform-:ethyl acetate:glacial acetic acid=30:10:1 or ethyl acetate-:toluene:glacial acetic acid=10:10:2).

2nd Step (debenzylation):

500 mg of the product formed in the 1st step were dissolved in a mixture of 9 ml ethanol and 1 ml glacial acetic acid, treated with 50 mg palladium on activated carbon (10% Pd) and stirred at 20° C. under normal pressure in a hydrogen atmosphere until the requisite stoichiometric amount of hydrogen had been absorbed (normally 4 to 6 hours). The reaction mixture was then filtered through celite, the solvent was distilled off, and the residue was dried under vacuum.

General Procedure for Examples 21, 24 and 26:

1st Step (acylation):

2 mmoles of the amino acid benzyl ester hydrochloride or tosylate were dissolved in 10 ml dichloromethane and treated with 4 mmoles triethylamine (8 mmoles in the case of diamino acid derivatives). A solution of 2 mmoles of 2,3-diacetoxybenzoyl chloride (4 mmoles for diamino acid derivatives) in 10 ml dichloromethane was slowly added drop-wise at −30° C. The reaction mixture was then stirred for a further 1 hour at −30° C. and for 1 hour at 20–25° C. The reaction solution was washed in succession with 1 M hydrochloric acid, saturated aqueous sodium hydrogen carbonate solution and saturated aqueous sodium chloride solution. The organic phase was dried over sodium sulphate, the solvent was removed under vacuum, and the residue was purified by recrystallisation from ethanol or toluene (in the case of the serine derivative) or by column chromatography (lysine derivative: silica gel 60, mobile phase:ethyl acetate:toluene=2:1).

2nd Step (cleavage of benzyl ester):

1 g of the product formed in the 1st step was dissolved in a mixture of 20 ml ethanol and 1 ml glacial acetic acid, treated with 100 mg palladium on activated carbon (10% Pd) and stirred for 2 hours at 20° C. under normal pressure in a hydrogen atmosphere. The reaction product was filtered through celite and the solvent was removed under vacuum. The residue was taken up in ethyl acetate and washed with saturated aqueous sodium chloride solution, and the organic phase was dried over sodium sulphate. After removing the solvent under vacuum, the product crystallised out or was purified by recrystallisation.

Example 18

L-2,5-bis-(2,3-Dihydroxybenzoylamino)-pentanoic Acid (18)

Formula I, where $R^1$=OH, $R^2$=$R^{11}$ in the 3-position, and with $R^6$=$R^{12}$, n=3, $R^{15}$=2,3-OH, Y=OH, L-form, Substance (18) was obtained from L-ornithine monohydrochloride, in a yield of 66% theoretical, as a white solid.

¹H NMR (DMSO-d$_6$, δ in ppm): 7.41 (dd, 1 H, ArH), 7.27 (dd, 1 H, ArH), 6.92 (m, 2 H, ArH), 6.69 (m, 2 H, ArH), 4.46 (m, 1 H, CH-N), 3.36 (m, 2 H, CH$_2$), 1.84 (m, 2 H, CH$_2$), 1.65 (m, 2 H, CH$_2$).

Example 19

L-2-(2,3-Dihydroxybenzoylamino)-propionic Acid (19)

Formula I, where R$^1$=OH, R$^2$=R$^{11}$ in the 3-position, and with R$^6$=CH$_3$, Y=OH, L-form Substance (19) was obtained from L-alanine, in a yield of 88% theoretical, as a white solid.

¹H NMR (DMSO-d$_6$, δ in ppm): 7.40 (dd, 1 H, ArH), 6.94 (dd, 1 H, ArH), 6.72 (dd, 1 H, ArH), 4.44 (m, 1 H, CH), 1.42 (d, 3 H, CH$_3$).

Example 20

L-2-(2,3-Diacetoxybenzoylamino)-propionic Acid (20)

Formula I, where R$^1$=OCOCH$_3$, R$^2$=R$^{11}$ in the 3-position, with R$^6$=CH$_3$, Y=OH, L-form Substance (20) was obtained from L-alanine benzyl ester hydrochloride, in a yield of 75% theoretical, as colourless crystals with an f.p. of 109° to 111° C.

¹H NMR (DMSO-d$_6$, δ in ppm): 7.50 (dd, 1 H, ArH), 7.39 (m, 2 H, ArH), 4.33 (m, 1 H, CH), 2.29 (s, 3 H, CH$_3$CO), 2.23 (s, 3 H, CH$_3$CO), 1.34 (d, 3 H, CH$_3$).

Example 21

L-2,4-Bis-(2,3-dihydroxybenzoylamino)-butyric Acid (21)

Formula I, where R$^1$=OH, R$^2$=R$^{11}$ in the 3-position, with R$^6$=R$^{12}$, n=2, R$^{15}$=2,3-OH, Y=OH, L-form Substance (21) was obtained from L-2,4-diaminobutyric acid dihydrochloride, in a yield of 81% theoretical, as a grey-white solid.

¹H NMR (DMSO-d$_6$, δ in ppm): 7.42 (dd, 1 H, ArH), 7.27 (dd, 1 H, ArH), 6.94 (m, 2 H, ArH), 6.72 (m, 2 H, ArH), 4.48 (m, 1 H, CH-N), 3.42 (m, 2 H, CH$_2$-N), 2.21 (m, 1 H, CH$_2$), 2.05 (m, 1 H, CH$_2$).

Example 22

L-3-[2,6-Bis-(2,3-dihydroxybenzoylamino)]-hexanoyl-amino]-2-(2,3-dihydroxybenzoylamino)-propionic Acid (22)

Formula I, where R$^1$=OH, R$^2$=R$^{11}$ in the 3-position, with R$^6$=R$^{13}$, n$_1$=1, n$_2$=4, R$^{15}$=2,3-OH, Y=OH, L-form Substance (22) was obtained from L-2-amino-3-(2,6-diamino-hexanylamino)-propionic acid, in a yield of 70% theoretical, as a white solid.

¹H NMR (DMSO-d$_6$, δ in ppm): 7.42 (dd, 1 H, ArH), 7.26 (m, 2 H, ArH), 6.91 (m, 3 H, ArH), 6.69 (m, 2 H, ArH), 6.67 (m, 3 H, ArH), 4.55–4.28 (m, 3 H, CH-N, CH$_2$-N), 4.10–3.09 (m, 3 H, CH$_2$-N), 1.72 (m, 2 H, CH$_2$), 1.51–1.28 (m, 4 H, CH$_2$).

Example 23

L-2-[2,3-Diacetoxybenzoylamino)-3-hydroxypropionic Acid (23)

Formula I, where R$^1$=OCOCH$_3$, R$^2$=R$^{11}$ in the 3-position, with R$^6$=CH$_2$, OH, Y=OH, L-form Substance (23) was obtained from L-serine benzyl ester hydrochloride, in a yield of 53% theoretical, as colourless needles, with an f.p. of 165 to 168° C. (acetone/hexane).

¹H NMR (DMSO-d$_6$, δ in ppm): 7.59 (dd, 1 H, ArH), 7.42 (m, 2 H, ArH), 4.42 (m, 1 H, CH), 3.76 (m, 1 H, CH$_2$O), 2.29 (s, 3 H, CH$_3$CO), 2.28 (s, 3 H, CH$_3$CO).

Example 23a

L-3-Benzyloxy-2-(2,3-diacetoxybenzoylamino)-propionic Acid

Formula I, where R$^1$=OCOCH$_3$, R$^2$=R$^{11}$ in the 3-position, R$^6$=CH$_2$OCH$_2$ (C$_6$H$_5$), Y=OH, L-form.

This substance was obtained in the form of white crystals from O-benzyl-L-serine benzyl ester, analogously to substance 23, but with the use of palladium on activated carbon (10% Pd) and cyclohexadiene in step 2.

Example 24

D-2,5-Bis-(2,3-dihydroxybenzoylamino)-pentanoic Acid (24)

Formula I, where R$^1$=OH, R$^2$=R$^{11}$ in the 3-position, with R$^6$=R$^{12}$, n=3, R$^{15}$=2,3-OH, Y=OH, D-form Substance (24) was obtained from D-ornithine monohydrochloride, in a yield of 66% theoretical, as a white solid.

¹H NMR (DMSO-d$_6$, δ in ppm): 7.41 (dd, 1 H, ArH), 7.27 (dd, 1 H, ArH), 6.93 (m, 2 H, ArH), 6.70 (m, 2 H, ArH), 4.46 (m, 1 H, CH-N), 3.33 (m, 2 H, CH$_2$-N), 1.84 (m, 2 H, CH$_2$), 1.64 (m, 2 H, CH$_2$).

Example 25

1L-2,6-Bis-(2,3-diacetoxybenzoylamino)-hexanoic Acid (25)

Formula I, R$^1$=OCOCH$_3$, R$^2$=R$^{11}$ in the 3-position, with R$^6$=R$^{12}$, n=4, R$^{15}$=2,3-OCOCH$_3$, Y=OH, L-form Substance (25) was obtained from L-lysine benzyl ester ditosylate, in a yield of 71% theoretical, as a white solid.

¹H NMR (CDCl$_3$, δ in ppm, J in Hz): 7.65 (dd, J=1.9, 7.4, 1 H, ArH), 7.47 (dd, J=2.3, 7.2, 1 H, Ar-H), 7.32–7.22 (m, J=1.8, 7.3, 5 H, ArH, CONH), 6.59 (t, J=5.7, 1 H, CONH), 4.75 (m, J=5.2, 7.2, 1 H, CH-N), 3.38 (m, 2 H, CH$_2$-N), 2.34 (s, 3 H, CH$_3$CO), 2.30 (s, 3 H, CH$_3$CO), 2.30 (s, 3 H, CH$_3$CO), 2.29 (s, 3 H, CH$_3$CO), 1.99 (m, 1 H, CH$_2$), 1.85 (m, 1 H, CH$_2$), 1.60 (m, 2 H, CH$_2$), 1.28 (m, 2 H, CH$_2$).

e. Oxazolidine-carboxylic Acid Residues

Example 26

(S)-3-(2,3-diacetoxybenzoyl)-oxazolidine-4-carboxylic Acid (26)

Formula I, where R$^1$=OCOCH$_3$, R$^2$=R$^{14}$ in the 3-position, with Z=O, R$^{16}$=R$^{17}$=H, Y=OH, S-form L-serine (105 mg, 1 mmole) was dissolved in 0.5 ml of 2 M aqueous sodium hydroxide solution and was treated at 0° C. with 0.1 ml of aqueous formaldehyde solution (36.5%). The reaction mixture was allowed to stand for 24 hours at 0° C.; 84 mg (1 mmole) sodium hydrogen carbonate and 1 ml acetone were then added and the mixture was cooled to −5° C. 257 mg (1 mmole) 2,3-di(acetoxy)benzoyl chloride were then added in portions, with stirring. After stirring for 1 hour at −5° C. to 0° C., the reaction mixture was diluted with 10 ml water and extracted with diethyl ether. The aqueous phase was acidified to pH 2–3 with 1 M hydrochloric acid and extracted with diethyl ether again (3×20 ml). The organic phase was dried over sodium sulphate and the solvent was removed under vacuum. The product obtained was dried under vacuum. Yield: 263 mg (78% theoretical). White foam.

$^1$H NMR (CDCl$_3$, δ in ppm): 7.35–7.27 (m, 3 H, ArH), 4.90 (s, 2 H, O-CH$_2$-N), 4.82 (m, 1 H, CH), 4.39 (m, 1 H, CH$_2$), 4.28 (m, 1 H, CH$_2$), 2.33 (s, 3 H, CH$_3$), 2.31 (s, 3 H, CH$_3$).

f. Conjugates With Antibiotics

Example 27

N-[L-2-(2,3-Diacetoxybenzoylamino)-propionyl]-ampicillin (IUPAC nomenclature: 6-{2 -[2-(2,3-diacetoxybenzoylamino)-propionylamino]-2-phenyl-acetylamino}-3,3-dimethyl-7-oxo-4-thia-1-azabicyclo[3.2.0]heptane-2-carboxylic acid) (27)

Formula I, where $R^1$=OCOCH$_3$, $R^2$=$R^{11}$ in the 3-position, with $R^6$=CH$_3$ (L-form), Y=N-ampicillino 500 mg (1.62 mmoles) L-2-(2,3-diacetoxybenzoylamino)-propionic acid (substance 20) were dissolved in 15 ml tetrahydrofuran, and 0.18 ml (1.62 mmoles) N-methylmorpholine followed by 0.21 ml (1.62 mmoles) isobutyl chloroformate were added drop-wise thereto at –20° C. with stirring. After stirring for 1 hour, a solution of 565 mg (1.62 mmoles) ampicillin trihydrate in 5 ml of 80% tetrahydrofuran, which was cooled to 0° C., was added drop-wise. The mixture was stirred for 1 hour at –20° C. and for 1 hour at room temperature and was then concentrated under vacuum. Water and ethyl acetate were then added and the mixture was carefully acidified to pH 2 with 1 M hydrochloric acid. The mixture was thoroughly and rapidly shaken until everything had dissolved, and the ethyl acetate phase was separated, washed until neutral with aqueous common salt solution, and dried over sodium sulphate. After concentration under vacuum, precipitation was effected with petroleum ether. Yield of crude product: 1 g; purity according to HPLC (Europher 100-7): about 75%). Purification was effected by way of preparative HPLC (RP$_{18}$, acetonitrile/water=40:60+0.50 % trifluoroacetic acid, flow rate 10 ml/minute). The fractions which contained the product were immediately extracted with ethyl acetate, and the organic phase was washed with water, dried, concentrated and the product was precipitated with petroleum ether. Purity according to HPLC: 95%.

$^1$H NMR (300 MHz, CDCl$_3$, δ in ppm, J in Hz): 7.63 (dd, J=1.9, 7.4, ArH), 7.33–7.19 (m, 7H, Ar-H), 5.61 (m, J=4.1, 2 H, CH-N), 5.42 (d, J=4.1, 1 H, CH-S), 5.00 (m, J=7.3, 1 H, CH-Me), 4.29 (s, 1H, CH-COO), 2.30 (s, 3 H, CH$_3$CO), 2.27 (s, 3 H, CH$_3$CO), 1.43 (s, 3 H, CH$_3$), 1.40 (d, J=7.1, 3 H, CH$_3$), 1.37 (s, 3H, CH$_3$).

Example 28

N-[2-(2,3-Diacetoxybenzoylamino)-benzoyl]-ampicillin (IUPAC nomenclature: 6-{2-[2-(2,3-diacetoxybenzoylamino)-benzoylamino]-2-phenyl-acetylamino}-3,3-dimethyl-7-oxo-4-thia-1-azabicyclo[3.2.0]heptane-2-carboxylic acid) (28)

Formula I, where $R^1$=OCOCH$_3$, $R^2$=$R^{11}$ in the 3-position, $R^{18}$–$R^{20}$=H, with COY in the 2-position, Y=N-ampicillino 0.11 ml (1 mmole) N-methylmorpholine and a catalytic amount of 4-dimethylaminopyridine were first added at –20° C. to a solution of 357 mg (1 mmole) 2-(2,3-diacetoxybenzoylamino)-benzoic acid (substance 17) in 5 ml of absolute tetrahydrofuran, followed by the addition of 126 μl of isobutyl chloroformate with stirring. The mixture was stirred for 1 hour at –20° C., and then a solution of 371 mg (1 mmole) of the sodium salt of ampicillin in 3 ml of 80% tetrahydrofuran was added in portions. The mixture was stirred for 1 hour at –20° C. and for 2 hours at room temperature. The solvent was then distilled off under vacuum, and 20 ml water and 20 ml ethyl acetate were added to the residue. The mixture was carefully acidified to pH 3 with 1 M hydrochloric acid and was thoroughly shaken. The organic phase was separated, washed three times with aqueous common salt solution, and dried over sodium sulphate. After concentration, precipitation was effected with petroleum ether. Yield of crude product: 420 mg.

The crude product was separated by means of preparative HPLC (Nucleosil 7 C 18, Macherey & Nagel, mobile phase 50/50 acetonitrile/water+0.05% trifluoroacetic acid 2nd Fraction N-(2-(2,3-diacetoxybenzoylamino)-benzoyl-ampicillin Yield from 420 mg of crude product: about 90 mg, HPLC (Europher 100 C 18-7, mobile phase 60/40 acetonitrile/water+0.05% trifluoroacetic acid).

$^1$H NMR (DMSO-d$_6$, δ in ppm): 7.3–8.4 (m 12 H, ArH), 5.9 (d, 1 H, J=7.7 Hz, CH), 5.53 (q, 1 H, CH), 5.42 (d, 1 H, J=4.0 Hz, CH), 4.2 (s, 1 H, CH), 2.32, 2.24 (s, 2×3 H, CH$_3$), 1.40, 1.50 (s, 2×3 H, CH$_3$).

Example 29

N-(4-(2,3-Diacetoxybenzoylamino)-benzoyl-ampicillin (29)

Formula I, where $R^1$=OCOCH$_3$, $R^2$=$R^{10}$ in the 3-position, $R^{18}$–$R^{20}$=H, with COY in the 4-position, Y=N-ampicillino Substance (29) was obtained, analogously to substance 28, from 4-(2,3-diacetoxybenzoylamino)-benzoic acid (substance 17) and the sodium salt of ampicillin. The crude product was separated by means of preparative HPLC (Nucleosil 7 C 18, Macherey & Nagel, mobile phase 50/50 acetonitrile/water+0.05% trifluoroacetic acid.

$^1$H NMR (DMSO-d$_6$, δ in ppm): 7.3–7.9 (m 12 H, ArH), 5.9 (d, 1 H, α-CH), 5.53 (q, 1 H, 6-CH), 5.41 (d, 1 H, 7-CH), 4.2 (s, 1 H, 3-CH), 2.20, 2.28 (s, 2×3H, CH$_3$), 1.40, 1.52 (s, 2×3 H, CH$_3$).

Example 30

(S)-N-[3-(2,3-di-(Methoxycarbonyloxy)-benzoyl]-oxazolidin-4-oyl]-ampicillin (IUPAC nomenclature: (S)-6-(2-{3-(2,3-di-(methoxycarbonyloxy)-benzoyl)-oxazolidine-4-carbonyl]-amino)-2-phenylacetylamino)-3,3-dimethyl-7-oxo-4-thia-1-azabicyclo[3.2.0]heptane-2-carboxylic acid) (30)

Formula I, where $R^1$=OCOOCH$_3$, $R^2$=$R^{14}$ in the 3-position, with Z=O, $R^{16}$, $R^{17}$=H, (S-form), Y=N-ampicillino Substance 30 was obtained, analogously to substance 28, from (S-3-(2,3-di-(methoxycarbonyloxy-benzoyl)-oxazolidine4-carboxylic acid and ampicillin trihydrate.

Example 31

N-[L-2,6-bis-(2,3-diacetoxybenzoylamino)-hexanoyl]-ampicillin (IUPAC nomenclature: 6-{L-2-(2,6-bis-(2,3-diacetoxy-benzoylamino)-hexanoylamino]-2-phenylacetylamino}-3,3- dimethyl-7-oxo-4-thia-1-azabicyclo[3.2.0]heptane-2-carboxylic acid) (31)

Formula I, where $R^1$=OCOCH$_3$, $R^2$=$R^{11}$ in the 3-position, with $R^6$=$R^{12}$, n=4, $R^{15}$=2,3-OCOCH$_3$, (L-form), Y=N-ampicillino Substance 31 was obtained, analogously to substance 28, from L,2,6-bis-(2,3-diacetoxybenzoylamino)-hexanoic acid (substance 25) and ampicillin trihydrate.

Example 32

N-[L-3-Acetoxy-2-(2,3-diacetoxybenzoylamino)-propionyl]-ampicillin (IUPAC nomenclature: 6-{L-2-[3-acetoxy-2-(2,3-diacetoxybenzoylamino)-propionylamino]-2-phenylacetylamino}-3,3-dimethyl-7-oxo-4-thia-1-azabicyclo[3.2.0]heptane-2-carboxylic acid) (32)

Formula I, where $R^1$=OCOCH$_3$, $R^2$=$R^{11}$ in the 3-position, with $R^6$=CH$_2$COOCH$_3$ (L-form), Y=N-ampicillino Substance 32 was obtained, analogously to substance 27, from L-3-acetoxy-2-(2,3-diacetoxybenzoylamino)-propionic acid and ampicillin trihydrate. The purity of the crude product as determined by HPLC (Nucleosil 7 C 18, Macherey & Nagel, mobile phase 40/60 acetonitrile/water+ 0.05% trifluoroacetic acid, flow rate: 1 ml/min) was 85%.

Example 33

N-[L-2-(2,3-diacetoxybenzoylamino)-propionyl]-cephadroxil (IUPAC nomenclature: 7-{L-2-[2-(2,3-diacetoxybenzoylamino)-propionylamino]2-(4-hydroxyphenyl)-acetylamino-3-methyl-8-oxo-5-thia-1-azabicyclo[4.2.]oct-2-ene-2-carboxylic acid) (33)

Formula I, where $R^1$=OCOCH$_3$, $R^2$=$R^{11}$ in the 3-position, with $R^6$=CH$_3$ (L-form), Y=N-cephadroxil (33)

Substance 33 was obtained, analogously to substance 28, from L-2-(2,3-diacetoxybenzoylamino)-propionic acid (substance 20) and cephadroxil. Purification was effected by means of preparative HPLC (RP18, 30:70 acetonitrile/water+0.1% trifluoroacetic acid).

Compound (33) which was obtained had a purity of 91%.

Example 34

N-[L-3-Benzyloxy-2-(2,3-diacetoxy-benzoylamino)-propionyl]-ampicillin

Formula I, where with $R^1$=OCOCH$_3$, $R^2$=$R^{11}$ in the 3-position, $R^6$=CH$_2$OCH$_2$(C$_6$H$_5$), L-Form, Y=N-ampicillino This substance was obtained, analogously to substance 28, from L-3-benzyloxy-2-(2,3-diacetoxy-benzoylamino)-propionic acid (substance 23a) and ampicillin trihydrate.

Example 35

N-[L-2,6-bis-(2,3-diacetoxy-benzoylamino)-hexanoyl]-amoxicillin

Formula I, where $R^1$=OCOCH$_3$, $R^2$=$R^{11}$ in the 3-position, $R^6$=$R^{12}$, n=4, $R^{15}$=2,3-OCOCH$_3$, L-Form, Y=N-amoxicillino This substance was obtained, analogously to substance 28 from L-2,6-bis-(2,3-diacetoxybenzoylamino)-hexanoic acid (substance 25) and amoxicillin trihydrate, in a yield of 84% theoretical.

Example 36

N-[3,5-bis-(2,3-diacetoxy-benzoylamino)-benzoyl]-ampicillin

Formula I, where $R^1$=OCOCH$_3$, $R^2$=$R^{10}$ the 3-position, $R^{18}$=$R^{19}$=H. $R^{20}$=(2,3-diacetoxy)-benzoylamino in the 5-position, with COY in the 3-position, Y=N-ampicillino This substance was obtained, analogously to substance 28, from 3,5-bis-(2,3-diacetoxy-benzoylamino)-benzoic acid (substance 16b) and the sodium salt of ampicillin.

Example 37

N-{4-[(2,3-di-methoxycarbonyloxy-benzoyl)-methyl-amino]-benzoyl}-ampicillin

Formula I, where $R^1$=OCOOCH$_3$, $R^2$=$R^{10}$ in the 3-position, $R^{19}$=CH$_3$, $R^{18}$=$R^{20}$=H, COY in the 4-position, Y=N-ampicillino A solution of 280 mg 4-[(2,3-di-methoxycarbonyloxy-benzoyl)-methyl-amino]-benzoyl chloride (prepared from 4-[(2,3-di-methoxycarbonyloxy-benzoyl)-methyl-amino]-benzoic acid=substance 16a and phosphorus pentachloride) was added drop-wise at –5° C., with stirring, to a solution of 245 mg of the sodium salt of ampicillin in 5 ml of aqueous tetrahydrofuran (80% THF). The mixture was stirred for 1 hour at 0° C. and for 1 hour at 20° C. and was then concentrated under vacuum. The residue was then brought to pH 3 with 1 N hydrochloric acid and was extracted with ethyl acetate. The extracts were washed with aqueous sodium chloride solution and were dried over sodium sulphate. After extensive concentration by evaporation, the batch was treated with petroleum ether. 425 mg (88% theoretical) of the title compound were thereby precipitated in the form of a white powder.

Na Salts of Substances 27, 28, 30, 31, 35 and 37

The sodium salts of the aforementioned substances could be obtained by die following general procedure:

A solution of 1.1 g of the acid in 5 ml ethyl acetate was treated with a solution of 0.5 g sodium 2-ethyl-hexanoate in 3 ml ethyl acetate and the mixture was diluted with 30 ml petroleum ether (boiling point 40–65° C.). The sodium salts which were thereby precipitated were isolated, dried under vacuum and purified by means of preparative HPLC in an RP 18 column. Yields: 50–80%

What is claimed is:

1. Catechol derivatives of general formula I

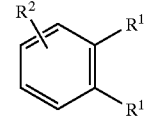

wherein the $R^1$ radicals denote O-acyl, and $R^2$ represents the following groups in the 3- and/or 4-position:
  amino acid residues:

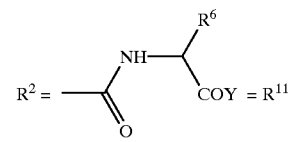

Y=OA, where A=H, alkyl, aryl, aralkyl, an alkali metal ion, an ammonium ion or a substituted ammonium ion, or Y=a residue of an antibacterial active ingredient which contains an OH or NH group, $R^6$=alkyl, $C_1$–$C_5$ hydroxyalkyl, or alkoxyalkyl, acyloxyalkyl, arylalkoxyalkyl, or

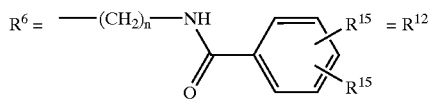

$R^{15}$ represents, identically to or independently of each other, H, OH, O-acyl, n is an integer between 1 and 5 when $R^{15}$ is H and/or O-acyl or

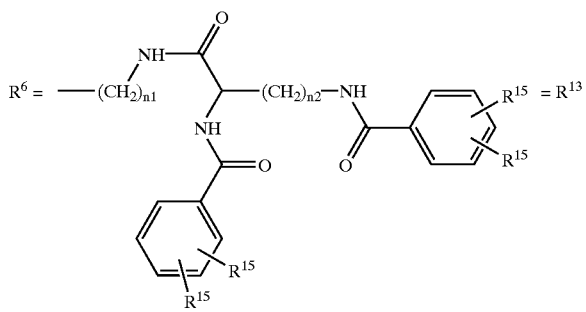

$R^{15}$=radicals which, identically to or independently of each other, denote H, OH, O-acyl, $n_1$ and $n_2$ represent an integer between 1 and 5.

2. Compounds of formula I according to claim 1, wherein $R^2$=$R^{11}$, with Y=OH, and $R^6$=a $C_1$–$C_4$ alkyl.

3. Compounds of formula I according to claim 1, wherein $R^2$=$R^{11}$, with Y=OH, $R^6$=$R^{12}$, and with $R^{15}$=O-acyl and n=1–5.

4. Compounds of formula I according to claim 1, wherein $R^2$=$R^{11}$, with Y=OH, $R^6$=$R^{13}$ with $R^{15}$=O-acyl and $n_1$ and $n_2$ denote an integer between 1 and 4.

5. Compounds of formula I according to claim 1, wherein Y is the residue of a cephalosporin.

6. Compounds of formula I according to claim 1, wherein Y is the residue of a penicillin.

7. Compounds of formula I according to claim 1, wherein Y is an ampicillin residue.

8. Compounds of formula I according to claim 1, wherein Y is an amoxicillin residue.

9. Compounds of formula I according to claim 1, wherein Y is a tetracycline residue comprising an NH or OH group.

10. Compounds of formula I according to claim 1, wherein Y is the residue of macrolide comprising an NH or OH group.

11. Compounds of formula I according to claim 1, wherein Y is the residue of a quinolone comprising an NH or OH group.

12. Compounds of formula I according to claim 1, wherein Y is the residue of a carbapenem comprising an NH or OH group.

13. Compounds of formula I according to claim 1, wherein $R^6$ is a $C_1$–$C_5$ alkyl or $C_1$–$C_5$ hydroxyalkyl.

14. The compound of general formula I according to claim 1, wherein the compound is L-2-(2,3-diacetoxybenzoylamino)-propionic acid.

15. The compound of general formula I according to claim 1, wherein the compound is L-2,6-bis-(2,3-diacetoxybenzoylamino)-hexanoic acid.

16. The compound of general formula I according to claim 1, wherein the compound is N-[L-2-(2,3-diacetoxybenzoylamino)-propionyl]-ampicillin.

17. The compound of general formula I according to claim 1, wherein the compound is N-[L-3-acetoxybenzoy-2-(2,3diacetoxy-benzoyl-amino)-propionyl]-ampicillin.

18. A pharmaceutical composition comprising a compound of formula I according to claim 1 and a pharmaceutically acceptable excipient or carrier.

19. A method of treating a patient suffering from a bacterial infection comprising administering to said patient an effective anti-bacterial amount of a compound of formula I according to claim 1.

* * * * *